(12) United States Patent
Mathieu et al.

(10) Patent No.: US 10,966,635 B2
(45) Date of Patent: Apr. 6, 2021

(54) INSOLES FOR INSERTION INTO AN ARTICLE OF FOOTWEAR AND SYSTEM FOR MONITORING A FOOT PRESSURE

(71) Applicant: FEETME, Versailles (FR)

(72) Inventors: Alexis Mathieu, Bonneuil Matours (FR); Andrey Mostovov, Paris (FR)

(73) Assignee: FEETME, Versailles (FR)

( * ) Notice: Subject to any disclaimer, the term of this patent is extended or adjusted under 35 U.S.C. 154(b) by 435 days.

(21) Appl. No.: 15/754,032

(22) PCT Filed: Aug. 25, 2015

(86) PCT No.: PCT/IB2015/001556
§ 371 (c)(1),
(2) Date: Feb. 21, 2018

(87) PCT Pub. No.: WO2017/033036
PCT Pub. Date: Mar. 2, 2017

(65) Prior Publication Data
US 2018/0256071 A1 Sep. 13, 2018

(51) Int. Cl.
*A61B 5/103* (2006.01)
*A43B 3/00* (2006.01)
(Continued)

(52) U.S. Cl.
CPC .......... *A61B 5/1036* (2013.01); *A43B 3/0005* (2013.01); *A43B 17/00* (2013.01);
(Continued)

(58) Field of Classification Search
CPC ..... A61B 5/6812; A61B 5/1038; A61B 5/112; A61B 5/1074; A61B 5/1036;
(Continued)

(56) References Cited

U.S. PATENT DOCUMENTS

| | | | |
|---|---|---|---|
| 2013/0213144 A1* | 8/2013 | Rice | A43B 3/0005 73/862.046 |
| 2016/0016041 A1* | 1/2016 | Giedwoyn | G16H 40/67 700/91 |

FOREIGN PATENT DOCUMENTS

| | | |
|---|---|---|
| DE | 102011012458 A1 | 8/2012 |
| DE | 102012004117 A1 | 9/2013 |

(Continued)

OTHER PUBLICATIONS

International Search Report related to Application No. PCT/IB2015/001556 dated Apr. 26, 2016.

*Primary Examiner* — Daniel L Cerioni
*Assistant Examiner* — Deirdre M Willgohs
(74) *Attorney, Agent, or Firm* — von Briesen & Roper, s.c.

(57) ABSTRACT

An insole for insertion into an article of footwear, comprising flexible upper sheet, lower sheet, insulating dielectric sheet, capacitive force sensors with upper electrodes and lower electrodes and networks of upper conductive leads and lower conductive leads. The insole comprises a chip support member and control and transmit electronics comprising a control electronic and a wireless transceiver.

An upper contacting tab of the upper sheet is in surface contact with the chip support member and comprises conductive leads connected to the upper electrodes. A lower contacting tab of the lower sheet is in surface contact with the chip support member and comprises conductive leads connected to the lower electrodes.

21 Claims, 7 Drawing Sheets

(51) Int. Cl.
*A61B 5/00* (2006.01)
*G01L 1/14* (2006.01)
*A43B 17/00* (2006.01)
*A43B 17/02* (2006.01)

(52) U.S. Cl.
CPC ............ *A43B 17/02* (2013.01); *A61B 5/6807* (2013.01); *G01L 1/146* (2013.01); *A61B 2562/0247* (2013.01)

(58) Field of Classification Search
CPC ..... A61B 5/6807; A43B 3/0005; A43B 17/00; A43B 17/006; A43B 17/02
USPC .......................... 600/592, 300, 301, 587, 595
See application file for complete search history.

(56) References Cited

FOREIGN PATENT DOCUMENTS

| | | |
|---|---|---|
| WO | WO 2009/070782 A1 | 6/2009 |
| WO | WO 2009/089406 A2 | 7/2009 |
| WO | WO 2016/009151 A1 | 1/2016 |

\* cited by examiner

INSOLES FOR INSERTION INTO AN ARTICLE OF FOOTWEAR AND SYSTEM FOR MONITORING A FOOT PRESSURE

CROSS-REFERENCE TO RELATED APPLICATION

This Application is a 35 USC § 371 US National Stage filing of International Application No. PCT/IB2015/001556 filed on Aug. 25, 2015.

FIELD OF THE DISCLOSURE

The invention is generally related to the monitoring of foot pressure. More particularly, the invention relates to Insoles for monitoring foot pressure and systems for monitoring foot pressure comprising such insoles.

BACKGROUND OF THE DISCLOSURE

In medical fields or sport training, it is often desirable to know the distribution of pressure forces exerted by the feet of a person, in a static or dynamic manner.

For instance, in the medical field, foot pressure monitoring could find applications as sole diagnostic podiatry or orthopaedics. By allowing a continuous monitoring of abnormal foot pressures, a system for monitoring foot pressure could also improve the prevention of foot lesions for diabetic patient with neuropathy.

In sports, a foot pressure monitoring insole, worn by a sportsman and connected to a remote server, could allow the athlete to quantify his or her moves and improve his or her performances.

Several systems and insoles for monitoring foot pressure are known.

For instance, WO 2009/070782 describes a force sensing system that can be used to sense pressure at a plurality of points of a user's foot and that comprise several transducers, processing means for processing the data acquired by the sensors and transmission means for transmitting the data to a remote server.

Document WO 2009/089406 also describes an insole including an array of pressure sensors together with signal processing means and a wireless transmitter able to relay the acquired signals to a remote.

However, these systems and insole present several drawbacks.

Under regular use, the insoles suffer strong stresses and structural constraints arising from the numerous bending cycles. Consequently, the connection between the electronic modules and the sensors quickly deteriorate and lead to malfunctions of the insole.

Moreover, the thicknesses of such insoles prevent an easy integration in various articles of footwear.

Processing modules, and in particular the connection means between electronic modules and sensors, are also often a source of discomfort for the user that hinders the adoption of such systems and insoles.

There are thus needs for systems and insoles for monitoring foot pressure that would be reliable in the long time, that would provide the user with a comfortable experience, could be easily switched between several articles of footwear, would have a low profile and/or a low cost.

There is also a need for insoles that can easily communicate with remote servers in order to quantify and analyse acquired data.

The instant invention has thus notably for object to improve this situation.

SUMMARY OF THE DISCLOSURE

A first object of the invention is thus an insole for insertion into an article of footwear, said insole being substantially planar and extending in an horizontal plane perpendicular to a thickness direction, the insole comprising a measurement portion extending in the horizontal plane, the measurement portion comprising at least:

a flexible upper sheet and a flexible lower sheet facing one another in the thickness direction;

a flexible insulating dielectric sheet arranged between the upper sheet and the lower sheet;

a plurality of capacitive force sensors in the measurement portion of the insole, each capacitive force sensor comprising at least an upper electrode on the upper sheet and a lower electrode on the lower sheet, the lower electrode facing the upper electrode in the thickness direction and being separated from the lower electrode at least by the flexible insulating dielectric sheet;

a network of upper conductive leads on the upper sheet, electrically connected to the upper electrodes of the plurality of capacitive force sensors, and a network of lower conductive leads on the lower sheet, electrically connected to the lower electrodes of the plurality of capacitive force sensors.

The insole is characterized in that it further comprises a chip portion extending in the horizontal plane, the chip portion comprising at least:

a chip support member being substantially planar and extending in the horizontal plane of the insole between an upper face and a lower face, said chip support member being separated from the dielectric sheet, and control and transmit electronics, mounted in the chip portion of the insole, and comprising at least a control electronic electrically connected to the plurality of capacitive force sensors and a wireless transceiver able to communicate with a remote server.

The insole is further characterized in that the upper sheet comprises an upper contacting tab extending from the measuring portion of the insole into the chip portion of the insole and being in surface contact with at least a portion of the chip support member, said upper contacting tab comprising at least one conductive lead connected to at least one upper electrode of a capacitive force sensor via the network of upper conductive leads, and the lower sheet comprises a lower contacting tab extending from the measuring portion of the insole into the chip portion of the insole and being in surface contact with at least a portion of the chip support member, said lower contacting tab comprising at least one conductive lead connected to at least one lower electrode of a capacitive force sensor via the network of lower conductive leads.

In some embodiments, one might also use one or more of the following features:

the insole extends along a longitudinal direction and along a transverse direction perpendicular to said longitudinal direction, said longitudinal direction and said transverse direction belonging to the horizontal plane of the insole, the insole has a length measured along the longitudinal direction and a width measured along transverse direction, the length of the insole being greater than the width of the insole, the upper contacting tab of the upper sheet extends from the measuring portion of the insole into the chip portion of the insole substantially along the transverse direction, and the lower contacting tab of the lower sheet extends from the measuring portion of the insole into the chip portion of the insole substantially along the transverse direction;

the chip support member is separated from the dielectric sheet by a gap, a minimal width of said gap between the chip support member, and the dielectric sheet, measured in the horizontal plane of the insole, being greater than 1 millimetre, preferably greater than 2 millimetres;

the chip portion of the insole further comprises a casing, the casing covering at least a majority of the upper face of the chip support member and/or at least a majority of the lower face of the chip support member;

the upper contacting tab of the upper sheet comprises at least one hole in the chip portion of the insole, and the lower contacting tab of the lower sheet comprises at least one hole in the chip portion of the insole;

the casing comprises at least one rod extending substantially along the thickness direction, said rod passing through said at least one hole of the upper contacting tab, through said at least one hole of the lower contacting tab, and through at least one hole of the chip support member;

the upper sheet comprises a plurality of upper contacting tabs extending from the measuring portion of the insole into the chip portion of the insole substantially along the transverse direction, the lower sheet comprises a plurality of lower contacting tabs extending from the measuring portion of the insole into the chip portion of the insole substantially along the transverse direction, and the chip portion of the insole and the measurement portion of the insole are mechanically connected to one another solely via the plurality of upper contacting tabs and the plurality of lower contacting tabs;

each upper contacting tab of the plurality of upper contacting tabs comprises at least one hole in the chip portion of the insole and each lower contacting tab of the plurality of lower contacting tabs comprises at least one hole in the chip portion of the insole;

the casing comprises a plurality of rods extending substantially along the thickness direction, each rod passing through at least one hole of an upper contacting tab of the plurality of upper contacting tabs, through at least one hole of a lower contacting tab of the plurality of lower contacting tabs, and through at least one hole of the chip support member;

the upper contacting tab of the upper sheet is at least partially covered by an upper thickening layer arranged on an upper face of the upper contacting tab of the upper sheet, the lower contacting tab is at least partially covered by a lower thickening layer arranged on a lower face of the lower contacting tab of the lower sheet, and the upper thickening layer, the upper contacting tab, the chip support member, the lower contacting tab and the lower thickening layer are sandwiched between an upper retaining portion and a lower retaining portion of the casing;

the casing comprises an upper casing portion and a lower casing portion assembled together and sandwiching the chip support member and the control and transmit electronics;

the chip support member comprises a plurality of plated through holes;

each capacitive force sensor of the plurality of capacitive force sensors is associated with at least one plated through hole of the plurality of plated through holes, and each of said associated plated through holes is electrically connected, to at least one pin of a chip of the control electronic, and to at least one conductive lead connected to an associated electrode of the associated capacitive force sensor;

said chip of the control electronic is mounted on one of the upper surface and the lower face of the chip support member, and said conductive lead connected to an associated electrode of the associated capacitive force sensor is located on the other of said upper face and said lower face of the chip support member;

the dielectric sheet is free of plated through holes;

the upper contacting tab and the lower contacting tab are facing each other along the thickness direction, and at least a portion of the chip support member is sandwiched between the upper contacting tab and the lower contacting tab;

a lower face of the upper contacting tab is in surface contact with the upper face of the chip support member, and an upper face of the lower contacting tab is in surface contact with the lower face of the chip support member;

the upper contacting tab and the lower contacting tab are respectively fixed to the upper face and the lower face of the chip support member, in particular are glued or laminated on said upper face and said lower face;

the upper contacting tab covers a majority of the upper face of the chip support member, and/or the lower contacting tab covers a majority of the lower face of the chip support member;

the chip support member is a laminate comprising an upper section, a middle section and a lower section, the upper contacting tab is sandwiched between the upper section and the middle section, and in surface contact with said upper section and said middle section, and the lower contacting tab is sandwiched between the middle section and the lower section, and in surface contact with said middle section and said lower section;

the control and transmit electronics are soldered on the chip support member, in particular on at least one conductive trace of an upper face and/or a lower face of the chip support member;

the upper contacting tab comprising at least one conductive lead is connected to an upper electrical connector fixed on the upper face of the chip support member, in particular a zero insertion force electrical connector, and the lower contacting tab comprising at least one conductive lead is connected to a lower electrical connector fixed on the lower face of the chip support member, in particular a zero insertion force electrical connector;

the control and transmit electronics are soldered on the upper contacting tab and/or on the lower contacting tab;

the control and transmit electronics are mounted outside of an internal region defined between the upper sheet and the lower sheet in the thickness direction, in particular outside of a contacting internal region defined between the upper contacting tab and the lower contacting tab;

the chip support member comprises at least one inside layer having at least one conducting trace, in particular at least one inside layer respectively separated from an upper face and a lower face of the chip support member by respective insulating layers;

the upper sheet and the lower sheet, each have an upper face and an opposite lower face, the lower face of the upper sheet and the upper face of the lower sheet are in contact with the dielectric sheet in the measurement portion of the insole, the upper electrodes of the plurality of capacitive force sensors, the network of upper conductive leads and the at least one conductive lead of the upper contacting tab are located on the lower face of the upper sheet, the lower electrodes of the plurality of capacitive force sensors, the network of lower conductive leads and the at least one conductive lead of the lower contacting tab are located on the upper face of the lower sheet;

the chip support member is a rigid circuit board;

the chip support member is a flexible substrate comprising at least one flexible polymer film;

the insole further comprises at least one plane flexible battery being either superimposed on the upper face of the chip support member so that the upper contacting tab is at least partially sandwiched between the battery and said upper face, or superimposed on the lower face of the chip support member so that the lower contacting tab is at least partially sandwiched between the battery and said lower face;

in the measurement portion of the insole, the upper sheet and the lower sheet are insulating except for the networks of upper and lower conductive leads and the upper and lower electrodes of the capacitive force sensors;

the upper sheet and the lower sheet each have a single layer of conductive material;

the dielectric sheet is made in a material selected in a list comprising cork, micro-architectured cork, elastomer, rubber, urethane, silicone, butyl rubber, polymer, neoprene, polyurethane, polyisoprene, and urethane foam;

the upper sheet and the lower sheet comprise at least one layer of a material selected in a list comprising polyester, polyimide, polyethylene napthalate, Polyetherimide, fluropolymers and copolymers of the formers;

the insole has a thickness less than one centimetre, preferably less than 0.75 centimetres;

the insole comprises a front portion arranged to be engaged by a forefoot of the foot, a mid portion arranged to be engaged by a midfoot of the foot, and a rear portion arranged to be engaged by a hindfoot of the foot, and the chip portion of the insole is located in the mid portion of the insole;

the measurement portion of the insole is located at least in the front portion and in the rear portion of the insole;

the insole further comprises at least one capacitive force sensor located in the mid portion of the insole;

the insole further comprises an upper contacting layer on top of the upper sheet of the insole, the upper sheet of the insole being sandwiched between the upper contacting layer and the dielectric sheet in the measurement portion of the insole, said upper contacting layer being elastic and adapted to be engaged by a foot of a wearer.

Another object of the invention is a system for monitoring a foot pressure comprising:

an insole as detailed above and a remote server able to communicate with the wireless transceiver of the insole to receive pressure related data from the insole.

BRIEF DESCRIPTION OF THE DRAWINGS

Other characteristics and advantages of the invention will readily appear from the following description of several of its embodiments, provided as non-limitative examples, and of the accompanying drawings.

On the drawings.

On the different figures, the same reference signs designate like or similar elements.

DETAILED DESCRIPTION

Figure 1:
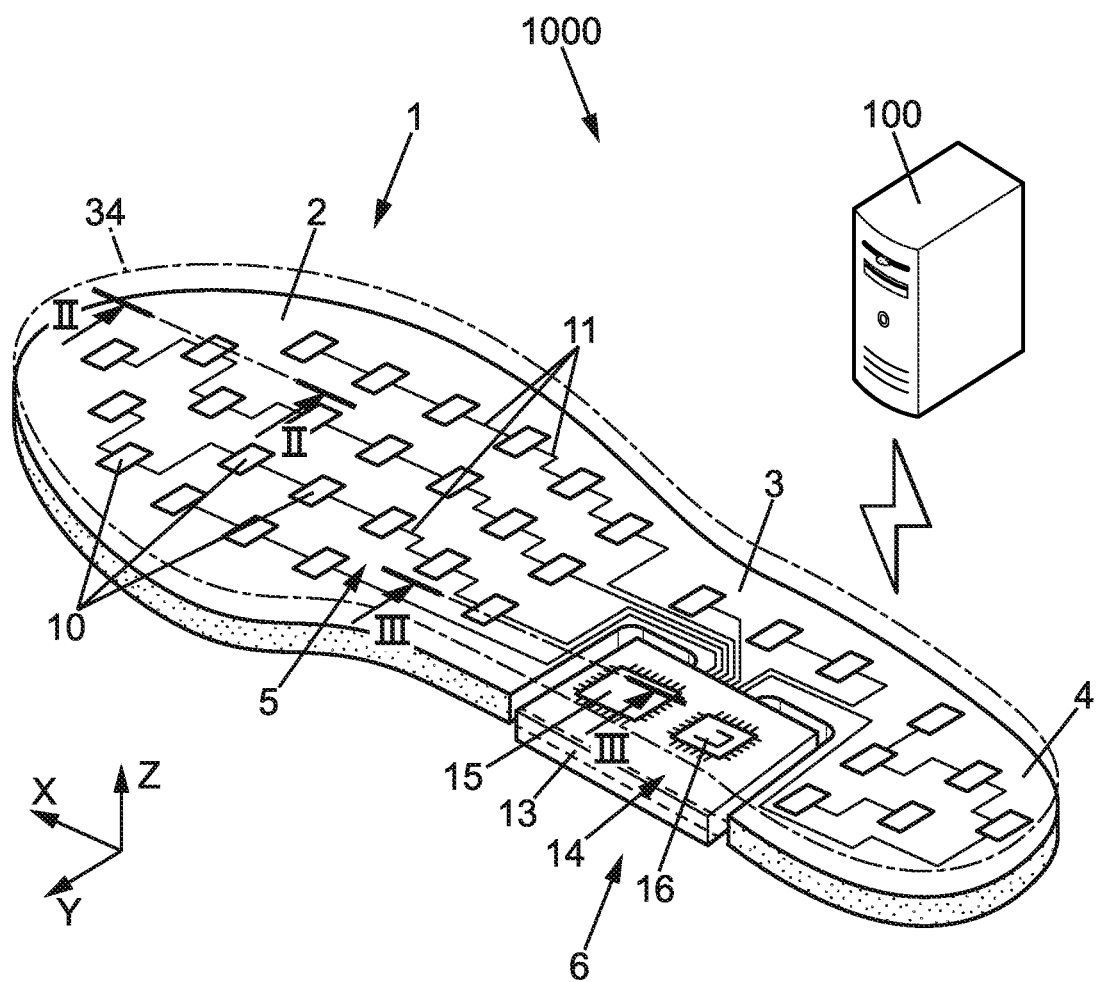
FIG. 1 is a schematic illustrating a system according to an embodiment of the invention comprising an insole according to an embodiment of the invention and a remote server.

The invention is susceptible of embodiment in many different forms. Preferred embodiments are shown in the drawings and herein described in details with the understanding that the present disclosure is to be considered as an exemplification of the principles of the invention. The present description and the drawings are not intended to limit the broad aspects of the invention to the embodiments illustrated and described.

Referring to FIG. 1, there is shown an insole 1 according to an embodiment of the invention.

The insole 1 is intended to be inserted into an article of footwear or included in the structure of the footwear. The article of footwear is for instance a shoe and can take many forms such that a street, athletic or orthopaedic shoe.

Insole 1 is substantially planar and extends perpendicularly to a thickness direction Z.

The insole 1 may thus extend between an upper insole surface 1a and a lower insole surface 1b, facing each other, both surfaces being perpendicular to the thickness direction Z.

By "substantially planar", it is understood that the insole extend generally along a plane, having large dimensions along a longitudinal direction X and a transverse direction Y (transverse direction Y being perpendicular to the longitudinal direction X), and a smaller dimension along a thickness direction Z that is perpendicular to the longitudinal and the transverse directions X, Y. Note that the insole may present structures, bumps and small curves and thus departs from a perfect plane. However, the extension of such structures, bumps and curves is understood to be small with comparison to the extension of the insole in the longitudinal and the transverse directions X, Y. For instance, the extension of the insole along the thickness direction Z may be at least ten times smaller than the extension of the insole 1 in the longitudinal and the transverse directions X, Y.

The longitudinal and the transverse directions X, Y form a plane denoted here as a "horizontal plane" X, Y.

More particularly, the insole 1 may extend mainly along the longitudinal direction X, secondly along the transverse direction Y. For instance, the insole has a length measured along the longitudinal direction X and a width measured along transverse direction Y, the length of the insole being greater than the width of the insole.

As a non-limitative example, the extension of the insole 1 along the transverse direction Y, called the "width", may be smaller than half of the extension of the insole 1 along the longitudinal direction X, called the "length".

In the present description the extension of the insole along the thickness direction Z is called "thickness". By "thickness", it is thus understood a maximal distance separating the upper insole surface 1a and the lower insole surface 1b of the insole 1, said distance being measured along the thickness direction Z.

The extension of the insole 1 along the thickness direction Z may be smaller than ten times the extension of the insole 1 along the longitudinal direction X. The extension of the insole 1 along the thickness direction Z may be smaller than several times the extension of the insole 1 along the transverse direction Y, for instance smaller than five times the extension of the insole 1 along the transverse direction Y.

The insole 1 may for Instance present a thickness of less than two centimetre, preferably less than 1.5 centimetres, for instance about 1 centimeters.

As illustrated on FIG. 1, the insole 1 can comprise a front portion 2 arranged to be engaged by a forefoot of a foot, a mid portion 3 arranged to be engaged by a midfoot of the foot, and a rear portion 4 arranged to be engaged by a hindfoot of the foot.

The front portion 2, the mid portion 3 and the rear portion 4 are connected together to form a single element that may be more or less flexible.

The front portion 2 may in particular extend on a larger dimension than the mid portion 3 along the transverse direction Y, i.e. the width of the front portion 2 may be greater than the width of the mid portion 3.

In a non-limitative example, the insole 1 can be a laminated sheet-like element with several stacked layers. This non limitative example will now be described, bearing in mind that alternative configuration may also be used within the context of the invention, for instance by inject polyurethane around the insole.

The configuration of layers of the insole 1 can in particular vary along its longitudinal and transverse extension as it will now be further detailed.

The insole 1 presents a measurement portion 5 and a chip portion 6.

The measurement portion 5 and the chip portion 6 have differing layers and differing layer arrangements.

In the embodiment of the invention illustrated on FIG. 1, the measurement portion 5 is located in the front portion 2 and in the rear portion 4 of the insole 1. The chip portion 6 is located in the mid portion 3 of the insole 1.

Alternatively, the measurement portion 5 may also comprise a portion of the mid portion 3 of the insole 1.

In some embodiment of the invention, the chip portion 6 may be located in the front portion 2 and/or in the rear portion 4.

Figure 2:
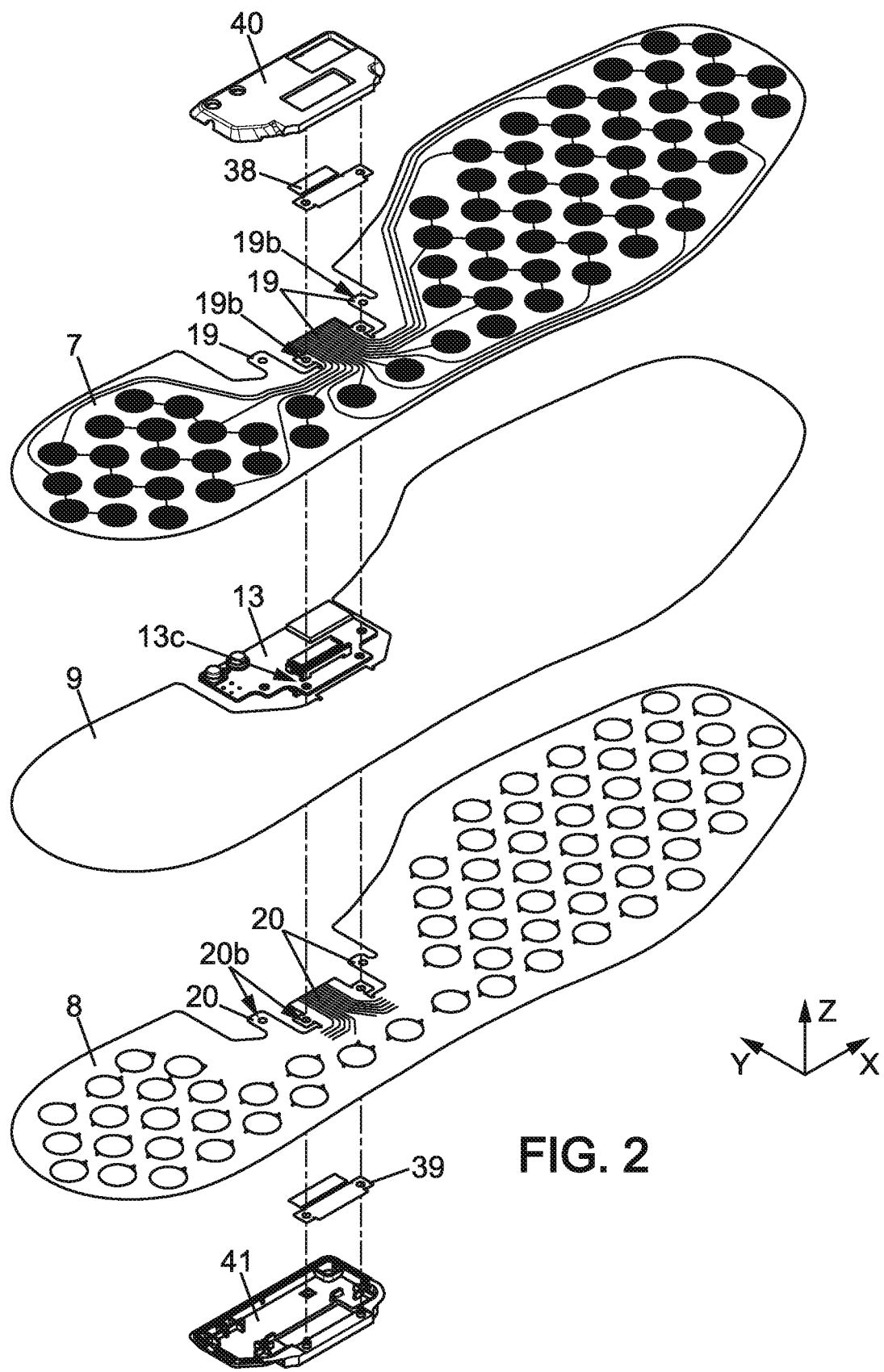
FIG. 2 is an exploded view of the insole of FIG. 1 illustrating an upper casing portion, an upper thickening layer, an upper sheet, a chip support member, a dielectric sheet, a lower sheet, a lower thickening layer and a lower casing portion.
Figure 3:
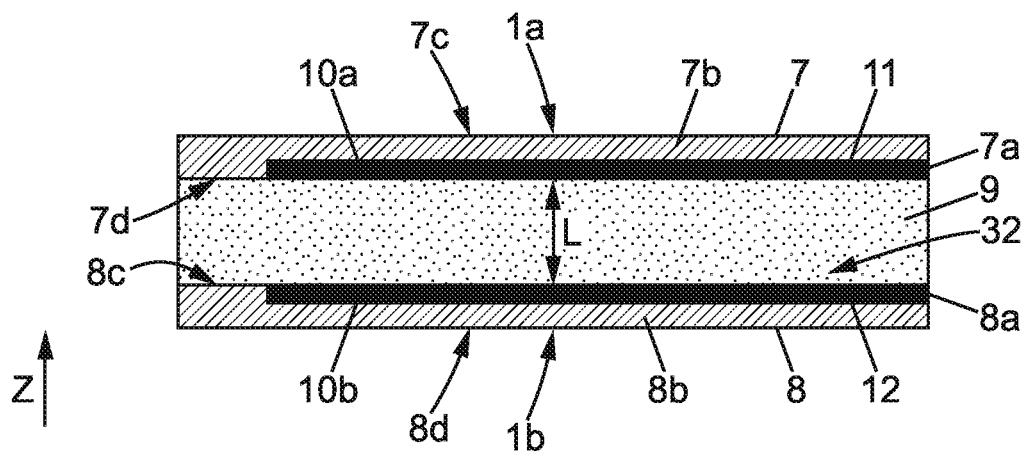
FIG. 3 is a detailed transverse section of a measurement portion of the insole of FIG. 1.
Figure 4:
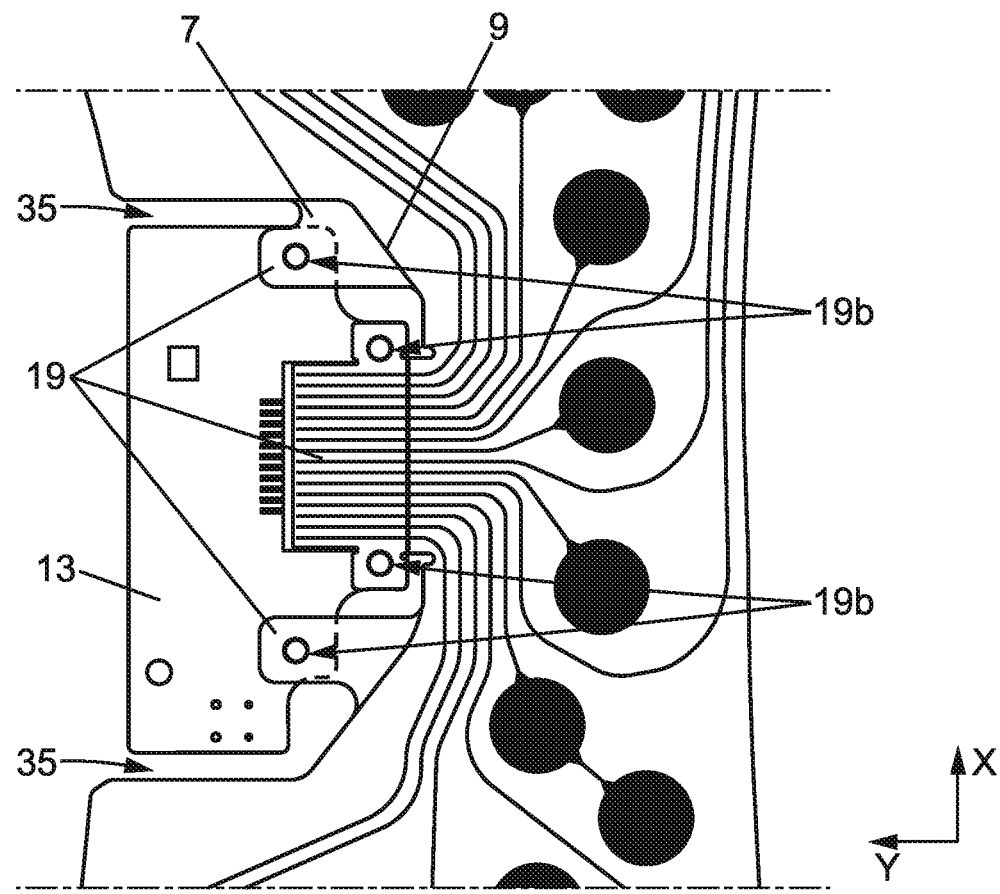
FIG. 4 is a detailed top view of a mid portion of the insole of FIG. 1, where the upper casing portion, the upper thickening layer and the upper sheet have been hidden to show in greater details the chip support member and the dielectric sheet in the chip portion of the insole.

Referring now to FIGS. 2 and 3, the configuration of the insole 1 in the measurement portion 5 will now be described in greater details.

In the measurement portion 5, the insole 1 comprises a flexible upper sheet 7 and a flexible lower sheet 8. The upper sheet 7 and the lower sheet 8 both extend generally along the longitudinal and transverse directions X, Y. The upper sheet 7 and the lower sheet 8 thus face each other in the thickness direction Z.

The insole 1 further comprises a dielectric sheet 9. The dielectric sheet 9 arranged between the upper sheet 7 and the lower sheet 8. The dielectric sheet 9 is advantageously a flexible insulating sheet as it will be detailed after.

As illustrated on FIGS. 1-4, a network of capacitive force sensors 10 is provided on the measurement portion 5 of the insole 1. The capacitive force sensors 10 are located in the front portion 2, the mid portion 3 and the rear portion 4 of the insole 1.

Referring more particularly to FIG. 3, each capacitive force sensor 10 comprises an upper electrode 10a on the upper sheet 7 and a lower electrode 10b on the lower sheet 8. The upper electrode 10a and the lower electrode 10b extend perpendicularly to the thickness direction Z and faces each other in the thickness direction Z.

The capacitive force sensors can be compression force and/or shear force sensors.

For example, the upper electrode 10a and the lower electrode 10b may be squares with about 5 mm sides, or may be disks with few millimetres diameters.

The upper electrode 10a and the lower electrode 10b are separated from each other at least by the dielectric sheet 9.

A network of upper conductive leads 11 is also provided on the upper sheet 7. The upper conductive leads 11 are electrically connected to the upper electrodes 10a of the capacitive force sensors 10. Similarly, a network of lower conductive leads 12 is provided on the lower sheet 8. The lower conductive leads 12 are electrically connected to the lower electrodes 10b of the capacitive force sensors 10.

In one embodiment of the invention, the upper conductive leads 11 and the lower conductive leads 12 may be arranged to connect separately each capacitive force sensor 10.

In another embodiment of the invention, the networks of upper conductive leads 11 and lower conductive leads 12 may be spatially multiplexed, i.e. arranged to be able to address each capacitive force sensor 10 separately by a combination of an upper conductive lead 11 and a lower conductive lead 12, for instance by addressing rows and columns in a matrix arrangement of the capacitive force sensors 10.

To this aim, the upper sheet 7 and the lower sheet 8 each comprise at least one conductive layer 7b, 8b. The upper sheet 7 and the lower sheet 8 also comprise each at least one insulating layer 7a, 8a.

The upper sheet 7 and the lower sheet 8 may be each provided with a single conductive layer 7b, 8b. In the embodiment of FIG. 3, the upper sheet 7 and the lower sheet 8 are each provided with a single insulating layer 7a, 8a.

Insulating layers 7a, 8a are made of insulating flexible polymer and may for instance be each made of a material selected in the list comprising polyester, polyimide, polyethylene napthalate, Polyetherimide, fluropolymers, mixed cells polyurethane foam and copolymers of the formers.

For instance, the insulating layers 7a, 8a may be made of a polyimide film such as Kapton. The insulating layers 7a, 8a are for instance kapton sheet with a thickness between 50 and 100 microns. The insulating layers 7a, 8a may have a dielectric constant of about 110 kV/mm.

The conductive layer 7b, 8b are electrically conductive and can be deposited on the insulating layers 7a, 8a or printed with an electrically conductive ink. The conductive layer 7b, 8b may be made or metal or conductive polymer for instance.

The conductive layer 7b of the upper sheet 7 comprises the upper electrodes 10a of the capacitive force sensors 10 and the network of upper conductive leads 11. Similarly, the conductive layer 8b of the lower sheet 8 comprises the lower electrodes 10b of the capacitive force sensors 10 and the network of lower conductive leads 12.

In one preferred embodiment of the invention, in the measurement portion 5 of the insole 1, the upper sheet 7 and the lower sheet 8 are insulating except for the conductive leads 11, 12 and the electrodes 10a, 10b of capacitive force sensors 10.

In the embodiment of the invention illustrated on FIG. 3, the insulating dielectric sheet 9 extends between an upper face 9a and a lower face 9b. The upper sheet 7, the dielectric sheet 9 and the lower sheet 8 are arranged in a coplanar staking arrangement as follows. The upper sheet 7 is laminated on the upper face 9a of the dielectric sheet 9 so that the conductive layer 7b is in surface contact with the upper face 9a of the dielectric sheet 9. On the other side of the dielectric sheet 9, the lower sheet 8 is laminated on the lower face 9b of the dielectric sheet 9 so that the conductive layer 8b is in surface contact with the lower face 9b of the dielectric sheet 9.

In other words, the upper sheet 7 and the lower sheet 8 each have respective upper faces 7c, 8c and respective lower faces 7d, 8d, facing the upper faces in the thickness direction Z. The conductive layer 7b of the upper sheet 7 is located on its lower faces 7d and the conductive layer 8b of the lower sheet 8 is located on its upper faces 8c.

The lower face 7d of the upper sheet 7 and the upper face 8c of the lower sheet 8 are thus in contact with the dielectric sheet 9 in the measurement portion 5 of the insole 1. The upper electrodes 10a of the capacitive force sensors 10 and the upper network of conductive lead 11 are then located on the lower face 7d of the upper sheet 7. The lower electrodes 10b of the capacitive force sensors 10 and the lower network of conductive lead 12 are located on the upper face 8c of the lower sheet 8.

Other embodiment can be envisaged wherein the conductive layers 7b, 8b and insulating layers 7a, 8a of the upper sheet 7 and the lower sheet 8 are arranged differently and, in particular are switched in the thickness direction Z.

In the absence of tensile or compressive loads or lateral shear, the value of the capacitance C of a capacitive force sensor 10 can be determined as a function of the thickness L of the dielectric sheet 9 at the location of the capacitive force sensor 10, the surface S of the upper electrode 10a and the lower electrode 10b and the dielectric constant ε of the material between the electrodes, in particular the dielectric sheet 9, in particular by the following equation:

$$C = \frac{\varepsilon S}{L}$$

Under the effect of a compressive or tensile load, the thickness L of the dielectric sheet 9 at the location of the capacitive force sensor 10 is changed and the capacitance C of the sensor 10 thus varies.

The thickness of the dielectric sheet 9 along the thickness direction Z may be in the range 0.2 mm to 1 mm.

The dielectric sheet 9 is advantageously made of a dielectric material which is resiliently deformable under tensile loads, compressive loads and lateral shearing. The mechanical resilience of a material elastomer can be defined as a ratio, often expressed as a percentage, of the energy returned after deformation divided by the energy used to deform the elastomer, under cyclic loading. The hysteresis rate corresponds to the dissipated energy and is thus the complement of the mechanical resilience. A high resilience can be associated to a low hysteresis.

The material of the dielectric sheet 9 can be selected depending on the application. The dielectric sheet 9 may for instance be made in a material selected in the list comprising cork, micro-architectured cork, elastomer, rubber, urethane, silicone, butyl rubber, polymer, neoprene, polyurethane, polyisoprene, and urethane foam.

In particular, the dielectric sheet 9 is made of an insulating material. The dielectric sheet may thus be made of a material that is neither conducting nor semi-conducting.

In a preferred embodiment, the dielectric sheet 9 remains within the flexible deformation range for applied pressures between 0 and 10 kg/cm (corresponding to the average of the plantar pressure) and the crushing of the material is preferably limited to between 10% and 50% of the thickness, preferably less than 50% when the applied pressure is 15 kg/cm.

This way, when the output capacity of the electrodes 10a, 10b is measured before and after the application of a compression load, it is possible to compute a variation in thickness L of the dielectric sheet 9 at the location of the capacitive force sensor 10.

In particular, it is then possible to compute a normal pressure, applied at the location of the capacitive force sensor 10, for instance by using for instance Hook's law which indicates that the normal strain σ applied to the surface of the dielectric sheet 9 is equal to the product of the percentage of thickness variation ΔL/L by the Young's modulus E of the material of the dielectric sheet 9:

$$\sigma = E \frac{\Delta L}{L}$$

The dielectric sheet 9 can for instance present a Young's modulus between 1 MPa and 5 MPa and a Poisson's ratio between 0 and 0.5 and preferably less than 0.1. Dielectric sheet 9 may have a dielectric constant between 3 and 10 kV/mm.

Turning now to FIGS. 4-11, the arrangement of the insole in the chip portion will now be described in greater details.

As illustrated on FIG. 1, the chip portion 6 of the insole extends substantially in the horizontal plane X, Y.

The chip portion 6 of the insole 1 comprises a chip support member 13.

The chip support member 13 is advantageously substantially planar and extends perpendicularly to the thickness direction Z of the insole 1, in the horizontal plane X, Y of the insole 1. The chip support member 13 thus extends between two opposite sides: an upper face 13a and a lower face 13b, facing each other in the thickness direction Z.

The chip support member 13 may present a thickness of the order of the thickness of the insole in the measurement portion 5 or slightly higher, in particular less than ten times the thickness of the insole in the measurement portion 3, in particular less than ten times the thickness of the dielectric layer 9.

In all the embodiments of the invention that are described, the chip support member 13 can be a rigid circuit board or can be a flexible substrate.

Such a rigid circuit board can comprise one or several non-conductive substrate(s). The rigid circuit board may further comprises one or several copper sheet(s) laminated onto the non-conductive substrate(s) and be a printed circuit board. The rigid circuit board can be a laminate and can comprise several conductive layers. The non-conductive substrate(s) may be for instance FR4 expoxy.

A flexible substrate can comprise at least one flexible polymer film, for instance one layer of a material selected in a list comprising polyester, polyimide, polyethylene napthalate, Polyetherimide, fluropolymers and copolymers of the formers. Conducting traces can be deposited on the polymer film as a layer or by ink printing. The flexible substrate can be a laminate of several polymer films with one or several conducting traces on said films.

As illustrated on FIGS. 4-11, the chip support member 13 is separated from the dielectric sheet 9.

More precisely, the chip support member 13 is separated from the dielectric sheet 9 by a gap 35.

By "separated by a gap", it is meant that the chip support member and the dielectric sheet are not in direct contact and can move one with respect to the other at least along the thickness direction. The gap 35 may be empty or may be filled by a flexible or soft material.

A minimal width of said gap 35, measured in the horizontal plane X, Y of the insole, can for instance be greater than 1 millimetre, preferably greater than 2 millimetres.

It should be noted that the measurement portion 5 of the insole 1 may also present one or several capacitive force sensors 10 on top or on the bottom of the chip portion 6 of the insole 1. To this aim, a pad of the measurement 5, comprising a portion of the flexible upper sheet 7, a portion of the flexible lower sheet 8 and a portion of the dielectric sheet 9, may for instance come over the chip portion 6 of the insole 1. Said pad may for instance be bended in the shape of a "S" in the vertical direction, t come over the chip portion 6. Said pad may extend from the rear, or from the front, of the insole 1. Advantageously, said pad may not be connected or fixed to the chip portion 6 to keep the mechanical connection between the measurement portion 5 and the chip portion 6 free from interferences. Alternatively, said pad may be fixed to the chip portion 6 in a small portion or said pad to guarantee an optimal position of the capacitive force sensors 10.

The chip portion 6 of the insole 1 also comprises control and transmit electronics 14.

The control and transmit electronics 14 are mounted in the chip portion 6 of the insole 1. The control and transmit electronics 14 can thus be located in close proximity with the chip support member 13 and in particular mounted on the chip support member 13 as detailed hereafter.

The control and transmit electronics 14 may include a control electronic 15 and a wireless, transceiver 16. The control electronic 15 comprises at least one chip 15a electrically connected to the capacitive force sensors 10. The wireless transceiver 16 is able to communicate with a remote server 100 as it will be detailed further below. In particular, the wireless transceiver 16 is connected to the control electronic 15 and is able to receive data from the control electronic 15 and transmit said data to the remote server 100 by wireless means (such as Wi-Fi, Bluetooth . . . ).

The insole 1 may be further provided with a battery 17 able to power the control and transmit electronics 14. The battery 17 can advantageously be a flexible battery.

The chip support member 13 can thus strengthen the insole 1 at the location of the control and transmit electronics 14 and allow the mounting of the control and transmit electronics 14 on the insole 1 in the chip portion 6 of the insole 1.

The electrical and mechanical connection between the chip portion 6 of the insole 1 and the measurement portion 5 of the insole will now be detailed.

The upper sheet 7 may be further provided with an upper contacting tab 19 and the lower sheet 8 is provided with a lower contacting tab 20.

The upper contacting tab 19 extends from the measuring portion 5 of the insole into the chip portion 6 of the insole 1. The upper contacting tab 19 may in particular extends substantially along the transversal direction Y.

The lower contacting tab 20 of the lower sheet 8 extends from the measuring portion 5 of the insole into the chip portion 6 of the insole 1. The lower contacting tab 20 may in particular extends substantially along the transversal direction Y.

The upper contacting tab 19 may extend from the measuring portion 5 of the insole over a distance of a few millimetres, in particular at least 5 millimetres, said distance being measured as an extension of the upper contacting tab 19 from the end of the dielectric sheet 9, i.e. from the beginning of the gap 35, in the horizontal plane X, Y.

Similarly, the lower contacting tab 20 may extend from the measuring portion 5 of the insole over a distance of a few millimetres, in particular at least 5 millimetres, said distance being measured as an extension of the lower contacting tab 20 from the end of the dielectric sheet 9, i.e. from the beginning of the gap 35, in the horizontal plane X, Y.

The upper contacting tab 19 and the lower contacting tab 20 are in surface contact with at least a portion of the chip support member 13. The upper contacting tab 19 thus presents at least one region of surface contact 21 with the chip support member 13. Similarly, the lower contacting tab 20 presents at least one region of surface contact 22 with the chip support member 13.

By "surface contact between the contacting portion and the chip support member", it is mean that each region of surface contact 21, 22 covers a bi-dimensional or tri-dimensional area and, in particular, extends along two respective perpendicular directions, on respective lengths that are larger than the thickness of the upper sheet and lower sheet. In some embodiments, the regions of surface contact 21, 22 may be buried inside the chip support member as illustrated on FIGS. 9-10.

The respective areas of said region of surface contact 21, 22 may be larger than a few square millimetres, for instance larger than 10 square millimetres.

Advantageously, the regions of surface contact 21, 22 both extend in the plane X, Y of the insole, i.e. perpendicular to the thickness direction Z.

The upper contacting tab 19 of the upper sheet 7 further comprises at least one conductive lead 19a. The conductive lead 19a is connected to at least one upper electrode 10a of a capacitive force sensor 10 via the network of upper conductive leads 11.

Similarly, the lower contacting tab 20 of the lower sheet 8 comprises at least one conductive lead 20a. The conductive lead 20a is connected to at least one lower electrode 10b of a capacitive force sensor 10 via the network of lower conductive leads 12.

The conductive lead 19a of the upper contacting tab 19 may belong to the region of surface contact 21 between the upper contacting tab 19 and the chip support member 13. The conductive lead 19a may thus be in contact with the chip support member 13 and, in particular, in extended contact with the chip support member 13.

The same way, the conductive lead 20a of the lower contacting tab 20 may belong to the region of surface contact 22 between the lower contacting tab 20 and the chip support member 13. The conductive lead 20a may thus be in contact, in particular, in extended contact, with the chip support member 13.

By "extended contact", it is for instance meant that the contact between each conductive lead 19a, 20a and the chip support member 13 extends over a length that is greater than the width of said conductive lead 19a, 20a. In particular, the contact between each conductive lead 19a, 20a and the chip support member 13 extends perpendicularly to the thickness direction Z, i.e. in the plane of the insole X, Y.

Said contact between each conductive lead 19a, 20a and the chip support member 13 may for instance extends over a length of a few millimetres, in particular at least 5 millimetres.

Figure 5:
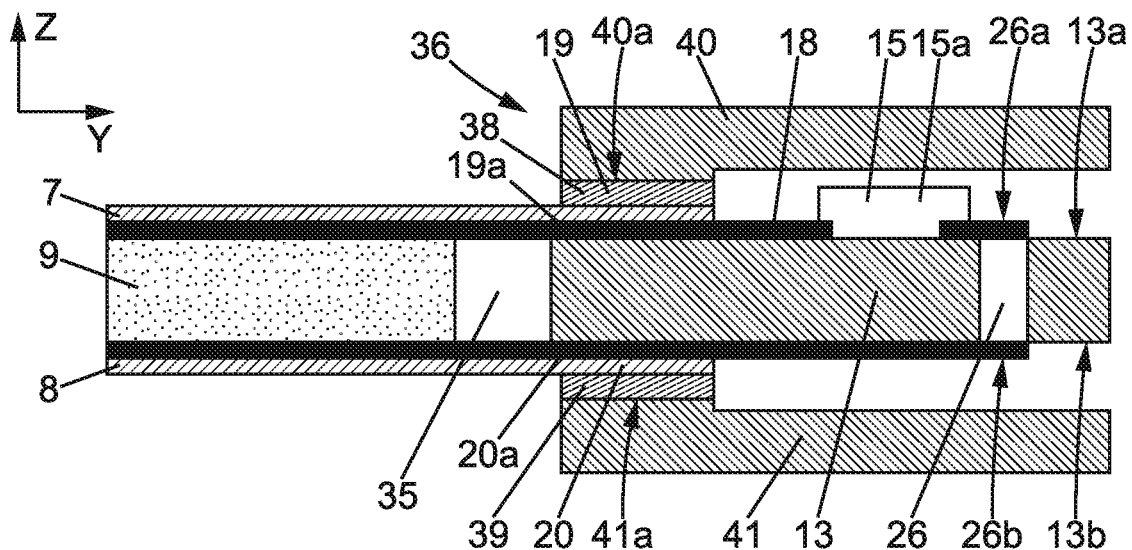
FIG. 5 is a detailed transverse section of a chip portion according to a first embodiment of an insole according to the invention.

FIG. 5 illustrates a first embodiment of the chip portion 6 of an insole 1 according to the invention.

On the example of FIG. 5, the chip support member 13 is provided with conductive tracks 18 on its upper face 13a and on its lower face 13b. In variant, conductive tracks 18 may be provided only on one of the upper face 13a and the lower face 13b.

The control and transmit electronics 14 are soldered on the chip support member 13, and in particular on the conductive tracks 18 provided on the chip support member 13.

In this first embodiment, the upper contacting tab 19 and the lower contacting tab 20 of the lower sheet are facing each other along the thickness direction Z.

The upper contacting tab 19 is in surface contact with the upper face 13a of the chip support member 13 and the lower contacting tab 20 is in surface contact with the lower face 13b of the chip support member 13.

In this embodiment, the whole thickness of the chip support member 13 is thus sandwiched between the upper sheet 7 and the lower sheet 8.

The upper contacting tab 19 and the lower contacting tab 20 are then respectively fixed to the upper face 13a and the lower face 13b of the chip support member 13.

In one embodiment, the upper contacting tab 19 and the lower contacting tab 20 can be for instance glued or laminated on said upper face 13a and lower face 13b.

Figure 6:
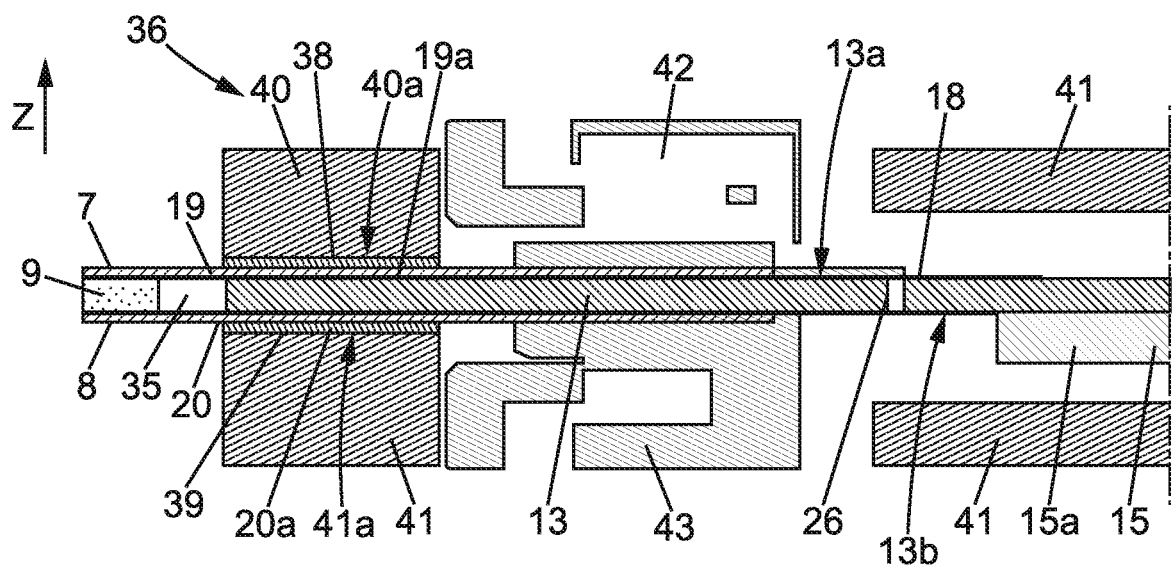
FIG. 6 is a detailed transverse section of a chip portion of a variant of the first embodiment of the insole illustrated on FIG. 5.
Figure 7:
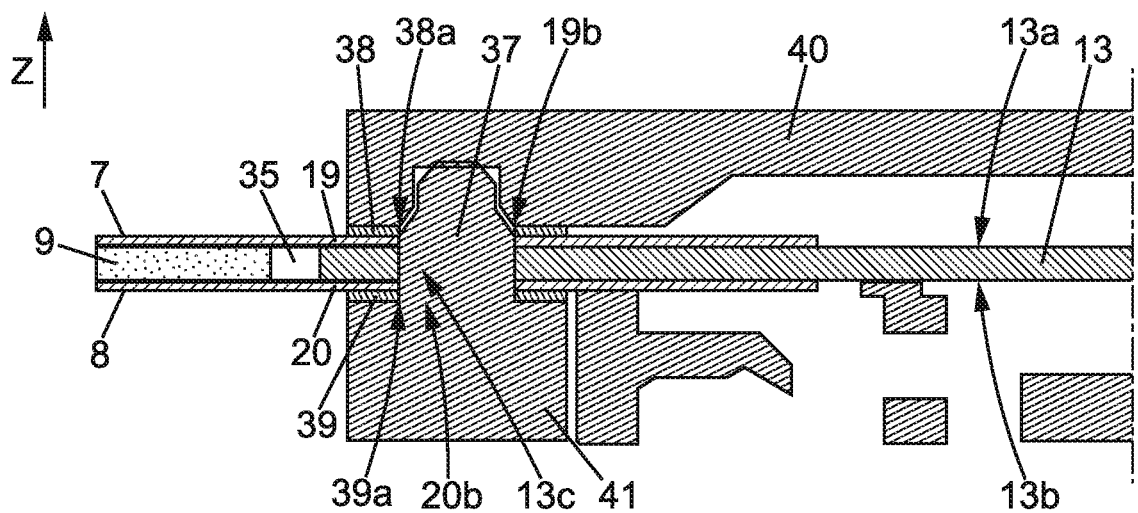
FIG. 7 is another detailed transverse section of the chip portion of the insole of FIG. 5, illustrating a rod of the casing passing through holes in the lower thickening layer, the lower contacting tab, the chip support member, the upper contacting tab and the upper thickening layer.

In the examples illustrated on FIGS. 6 and 7, the upper contacting tab 19 and the lower contacting tab 20 can be mechanically attached to the chip support member 13 in a removable way that will now be detailed. The variants illustrated on FIGS. 6 and 7 may combined together and with the variant of FIG. 5.

As illustrated on FIGS. 2 and 5-7, the chip portion 6 of the insole 1 may further comprises a casing 36.

The casing 36 may for instance covers at least a majority of the upper face 13a of the chip support member 13 and/or at least a majority of the lower face 13b of the chip support member 13.

The casing 36 can be for example a rigid plastic casing or a coating of polymer. The casing 36 may further comprise one or several openings, for instance an opening next the wireless transceiver 16 of the control and transmit electronics 14. This way the quality of wireless data transmit may be improved.

As illustrated on FIGS. 2 and 5-7, the casing 36 can comprise an upper casing portion 40 and a lower casing portion 41. The upper casing portion 40 and the lower casing portion 41 are assembled together, sandwiching the chip support member 13 and the control and transmit electronics 14.

On the one hand, the casing 36 may comprise one or several rods 37 extending substantially along the thickness direction Z that are illustrated on FIG. 7 in particular.

On the other hand, the upper contacting tab 19, the lower contacting tab 20 and the chip support member 13 may each comprise at least one hole 19b, 20b, 13c in the chip portion 6 of the insole 1.

The rod 37 of the casing 36 may then be arranged to pass through said hole 19b of the upper contacting tab 19, through said hole 20b of the lower contacting tab 20, and through said hole 13c of the chip support member 13 as illustrated on FIG. 7. This way it is possible to maintain the connecting tab.

To this aim, the hole 19b of the upper contacting tab 19, the hole 20b of the lower contacting tab 20, and the hole 13c of the chip support member 13 may be aligned along the thickness direction Z.

Moreover, the upper contacting tab 19 of the upper sheet 7 may be at least partially covered by an upper thickening layer 38. The upper thickening layer 38 may be arranged on the upper face 7c of the upper contacting tab 19 of the upper sheet 7.

Similarly, the lower contacting tab 20 may be at least partially covered by a lower thickening layer 39 arranged on a lower face 8d of the lower contacting tab 20 of the lower sheet 8.

The upper thickening layer 38 and the lower thickening layer 39 may be flexible or rigid plastic layers with a high tensile strength.

The upper thickening layer 38 and the lower thickening layer 33 may be each provided with respective holes 38a, 39a.

The rod 31 of the casing 36 may then be arranged to additionally pass through said holes 38a, 39a of the upper thickening layer 38 and the lower thickening layer 39.

In one embodiment of the invention, the upper contacting tab 19 comprises two holes 19a surrounding the conductive leads 19a of the upper contacting tab 19 in the longitudinal direction X. Similarly, the lower contacting tab 20 may comprise two holes 20a surrounding the conductive leads 20a of the lower contacting tab 20 in the longitudinal direction X. Said holes 19a, 20a may be penetrated by associated rods 37 of the casing 36 as detailed above.

As illustrated on FIGS. 2 and 5-11, the upper sheet 7 may be provided with a plurality of upper contacting tabs 19 extending from the measuring portion 5 of the insole into the chip portion 6 of the insole 1 substantially along the transversal direction Y.

Similarly, the lower sheet 8 may be provided with a plurality of lower contacting tabs 20 extending from the measuring portion 5 of the insole into the chip portion (6) of the insole 1 substantially along the transversal direction Y.

The plurality of upper contacting tabs 19 and the plurality of lower contacting tabs 20 may be such that the chip portion 6 of the insole 1 and the measurement portion 5 of the insole 1 are mechanically connected to one another solely via the plurality of upper contacting tabs 19 and the plurality of lower contacting tabs 20.

To this aim, each upper contacting tab of the plurality of upper contacting tabs 19 may comprise at least one hole 19b in the chip portion 6 of the insole and each lower contacting tab of the plurality of lower contacting tabs 20 may comprise at least one hole 20b in the chip portion 6 of the insole. The chip support member 13 may also comprises a plurality of holes 13c.

The casing 36 may then comprise a plurality of rods 37 extending substantially along the thickness direction Z and associated to said plurality of upper contacting tabs 19, to said plurality of lower contacting tabs 20 and to said plurality of holes 13c of the chip support member 13. Each rod 37 of the plurality of rods 37 may then pass through one hole 19a of an upper contacting tab 19 of the plurality of upper contacting tabs 19, through one hole 20b of a lower contacting tab 20 of the plurality of lower contacting tabs 20, and through one hole 13c of the plurality of holes 13c of the chip support member 13.

This way the relative movements of chip support member 13 and the dielectric sheet 9 can be limited at least in the horizontal plane X, Y of the insole 1.

Moreover, the upper casing portion 40 may be provided with an upper retaining portion 40a. The lower casing portion 41 may be provided with a lower retaining portion 41a. The upper retaining portion 40a and the lower retaining portion 41a may be facing each other in the thickness direction Z and be arranged so that the upper thickening layer 38, the upper contacting tab 19, the chip support member 13, the lower contacting tab 20 and the lower thickening layer 39 are sandwiched between said upper retaining portion 40a and lower retaining portion 41a.

Such an arrangement of the casing 36 ensures that the mechanical efforts between the chip portion 6 and the measurement portion 5 of the insole 1 are not transmitted to the electrical connection of the upper contacting tab 19 and the lower contacting tab 20.

Turning to the electrical connection between the measurement portion 5 and the chip portion 6 of the insole, FIG. 5 illustrates a first variant of the invention.

In this variant, the conductive leads 19a of the upper contacting tab 19 are located on the lower face 7d of the upper sheet 7 and are in extended contact with at least one conductive track 18 located on the upper face 13a of the chip support member 13.

The conductive leads 19a may then be soldered to respective conductive tracks 18 of the chip support member 13.

Similarly, the conductive leads 20a of the lower contacting tab 20 are located on the upper face 8c of the lower sheet 8 and are in extended contact with at least one conductive track 18 located on the lower face 13b of the chip support member 13.

The conductive leads 20a may then be soldered to respective conductive tracks 18 of the chip support member 13 or fixed using Z axis tape for instance.

In a variant illustrated on FIG. 6, the conductive leads 19a of the upper contacting tab 19a re electrically connected to respective conductive tracks 18 of the chip support member 13 through an upper electrical connector 42 fixed on the upper face 13a of the chip support member 13.

Similarly, in the variant of FIG. 6, the conductive leads 20b of the lower contacting tab 20 are electrically connected to respective conductive tracks 18 of the chip support member 13 through a lower electrical connector 43 fixed on the lower face 13a of the chip support member 13.

The upper electrical connector 42 and the lower electrical connector 43 may for instance be zero insertion force electrical connectors, i.e. connectors that requires very little force for insertion.

This way, the mechanical and electrical connection between the measurement portion 5 and the chip portion 6 of the insole may be removable connections allowing changing the chip portion 6 without damaging the insole.

As illustrated on FIG. 5, the chip support member 13 may also advantageously comprise a plurality of plated through holes 26.

The plated through holes 26 are conductive links that respectively extend between upper ends 26a and lower ends 26b. The plated though holes can be holes drawn through the chip support members 13 that are plated with an electrically conductive layer such as a metal.

In a preferred embodiment of the invention, the dielectric sheet 9 is free of plated through holes. The dielectric sheet 9 is thus insulating.

In the embodiment of FIG. 5, the upper ends 26a are located on the upper face 13a of the chip support member 13 and the lower ends 26b are located on the lower face 13b of the chip support member 13.

Between its upper end 26a and its lower end 26b, a plated through holes 26 may intersect layers of the chip support member or of the upper or lower sheet 7, 8 and be electrically connected with said layers as it will be detailed hereafter. These intermediate connections are referred by reference numeral 26c and are further detailed in hereafter in reference to FIGS. 9 and 10.

Each capacitive force sensor 10 is associated with at least one plated through hole 26. More precisely, an associated plated through hole 26 is electrically connected to at least one pin of a chip 15a of the control electronic 15 and to at least one conductive lead connected to an electrode of the associated capacitive force sensor 10.

In one preferred embodiment, the plated through hole 26 is connected to the chip 15a on one end, the upper end 26a or the lower end 26b, and is electrically connected to the associated capacitive force sensor 10 either on the other end 26b, 26a, or by an intermediate connection 26c.

This way a reliable electrical connection can be made between the capacitive force sensors 10 and the control and transmit electronic 14. The electrical connection further presents a small extension along the thickness direction which improves the comfort for the wearer. The electrical connection is also more resistant to stresses and structural constraints arising from the numerous bending cycles.

To set these ideas on a non-limitative example, illustrated on FIG. 5, the chip 15a can be mounted on the upper insole surface 1a of the insole 1. A plated through hole 26 can then be electrically connected to a pin of chip 15a on its upper end 26a, and be electrically connected to a lower electrode 10b of a capacitive force sensor 10 on its lower end 26b.

In a variant illustrated on FIG. 6, the chip 15a is mounted on the lower face 13b of the chip support member 13 and said plated through hole 26 is connected to an upper electrode 10a of the associated capacitive force sensor 10 on its upper end 26a, and to the chip 15a on the lower end 26b.

Figure 8:
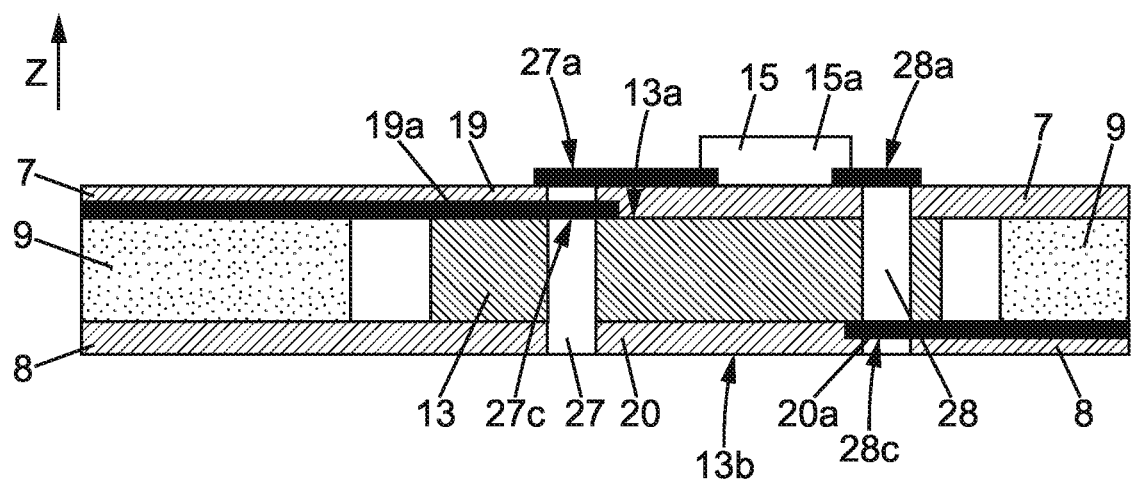
FIG. 8 is a detailed transverse section of a chip portion of a second embodiment of an insole according to the invention.

FIG. 8 illustrates a second embodiment of the invention wherein the upper contacting tab 19 covers a majority of the upper face 13a of the chip support member 13 and the lower contacting tab 20 covers a majority of the lower face 13b of the chip support member 13.

In the example of FIG. 8, the upper contacting tab 19 entirely covers the upper face 13a of the chip support member 13 and the lower contacting tab 20 entirely covers the lower face 13b of the chip support member 13.

In this embodiment of the invention, the control and transmit electronics 14 are soldered on the upper contacting tab 19 and/or on the lower contacting tab 20.

In this second embodiment, the upper sheet 7 in particular comprises two conductive layers 7b, one on its upper face 7c and one on its lower face 7d.

The control and transmit electronic is soldered on the conductive layer 7b on the upper face 7c of the upper sheet 7. The conductive leads 19a connected to the upper electrodes 10a of the capacitive force sensors 10 are located on the lower face 7d of the upper sheet 7.

One or several plated through holes 26 may then electrically connect the two conductive layers 7b of the upper sheet 7 as detailed above.

In a non-illustrated variant, the lower contacting tab 20 may be provided with two conducting layers 8b and arranged in a similar way to the upper contacting tab 19.

Figure 9:
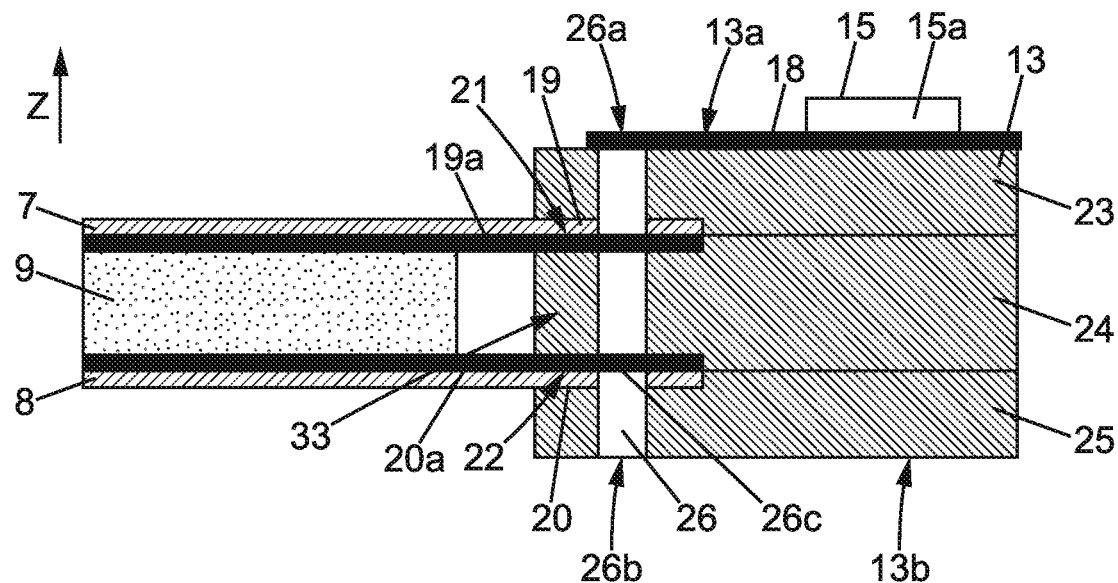
FIG. 9 is a detailed transverse section of a chip portion of a third embodiment of an insole according to the invention.

FIG. 9 illustrates a third embodiment of the invention wherein only a portion of the thickness of the chip support member 13 is sandwiched between the upper and lower contacting tabs 19, 20.

To this aim, the chip support member 13 can be, for instance, a laminate comprising an upper section 23, a middle section 24 and a lower section 25.

The upper contacting tab 19 and the lower contacting tab 20 are laminated within the chip support member 13, between said upper section 23, middle section 24 and a lower section 25.

More precisely, the upper contacting tab 19 of the upper sheet 7 is sandwiched between the upper section 23 and the middle section 24 of the chip support member 13. The upper contacting tab 19 is thus in surface contact with the upper section 23 and with the middle section 24 of the chip support member 13. The upper face 7c of the upper contacting tab 19 is thus in surface contact with the upper section 23, and the lower face 7d of the upper contacting tab 19 is in surface contact with the middle section 24. The lower contacting tab 20 of the lower sheet 8 is sandwiched between the middle section 24 and the lower section 25 of the chip support member 13. The lower contacting tab 20 is thus in surface contact with the middle section 24 and the lower section 25 of the chip support member 13. More precisely, the upper face 8c of the lower contacting tab 20 is in surface contact with the middle section 24, and the lower face 8d of the lower contacting tab 20 is in surface contact with the lower section 25 of the chip support member 13.

In the example of FIG. 9, a plated through hole 26 crosses the lower contacting tab 20, the chip support member 13 and the upper contacting tab 19.

In this example there are two type of plated through holes 26, respectively referred by reference numerals 27 and 28.

A plurality of first plated through holes 27 are connected to the upper electrodes 10a of the capacitive force sensors 10. The first plated through holes 27 are connected to the upper electrodes 10a by respective intermediate connections 27c with respective conductive leads 19a of the upper contacting tab 19 of the upper sheet 7.

A plurality of second plated through holes 28 are connected to the lower electrodes 10b of the capacitive force sensors 10. The second plated through holes 28 are connected to the lower electrodes 10b by intermediate connections 28c with respective conductive leads 20a of the lower contacting tab 20 of the lower sheet 8.

In the example of FIG. 9, the control electronic 15 is located on the upper face 13a of the chip support member 13.

Both first plated through holes 27 and second plated through holes 28 are thus connected to the chip 15a at their upper ends 27a, 28a.

Figure 10:
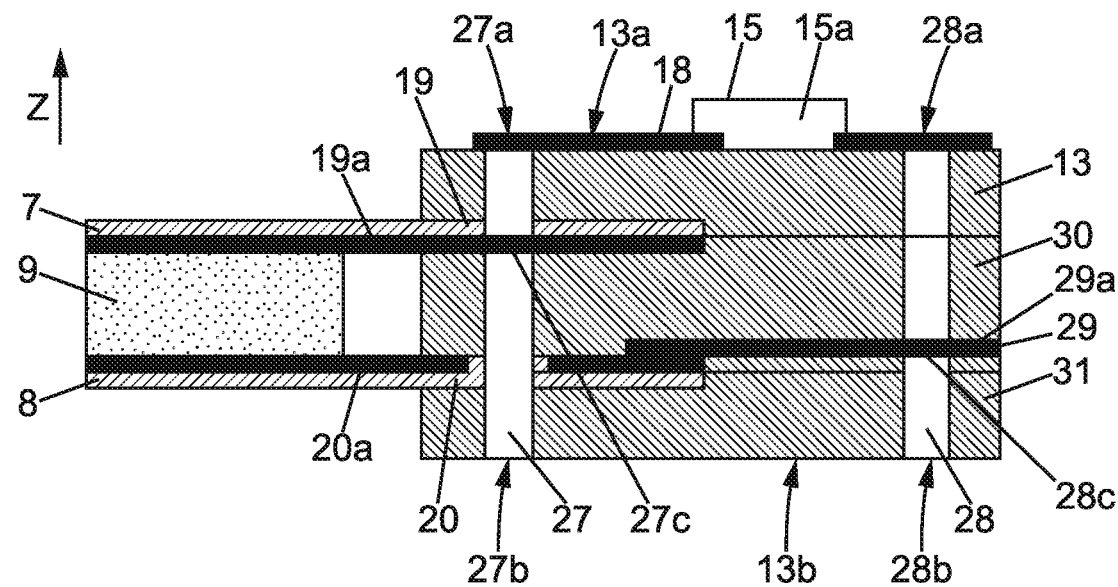
FIG. 10 is a detailed transverse section of a chip portion of a forth embodiment of an insole according to the invention.

FIG. 10 illustrates a forth embodiment of the invention wherein the chip support member 13 comprises at least one inside layer 29 having at least one conducting trace 29a.

The inside layer 29 extend perpendicularly to the thickness direction 13 and is located between the upper face 13a and the lower face 13b of the chip support member 13. The inside layer 29 is thus for instance separated, respectively from the upper face 13a and the lower face 13b of the chip support member 13, by respective insulating layers 30, 31.

In the embodiment of FIG. 10, the conductive leads 19a of the upper contacting tab 19 are connected to the conducting trace 29a of the inside layer 29, for instance, by soldering.

A plated through hole 26 electrically connected to the inside layer 29 by an intermediate connections 26c may then provide an electrical connection between the conductive leads 19a of the upper contacting tab 19 and the chip 15a as detailed above.

In other embodiments, not illustrated on the drawings, the conductive leads 20a of the lower contacting tab 20 may also be connected to the conducting trace or traces 29a of an inside layer 29, for instance, by soldering.

The chip support member 13 may be provided with two or more inside layers 29 that present the same characteristics as detailed above.

As illustrated on the figures, in several embodiments of the invention, the control and transmit electronics 14 are mounted outside of an internal region 32 that may be defined, in the thickness direction Z, between the upper sheet 7 and the lower sheet 8.

By "mounted outside of the internal region", it is meant that no chip of the control and transmit electronics 14 is located in the internal region separating the upper sheet and the lower sheet.

In particular, the control and transmit electronics 14 may be mounted on the upper insole surface 1a and/or the lower insole surface 1b.

In the illustrated embodiments of the invention, the control and transmit electronics 14 may be mounted outside of a contacting internal region 33 defined between the upper contacting tab 19 and the lower contacting tab 20.

In some embodiments of the invention that are not illustrated on the drawings, the control and transmit electronics 14 may be mounted inside, or at least partially inside, the chip support member 13.

By "inside", it is meant that at least one chip of the control and transmit electronics 14 may be located between the upper face 13a and the lower face 13b of the chip support member 13.

Figure 11:
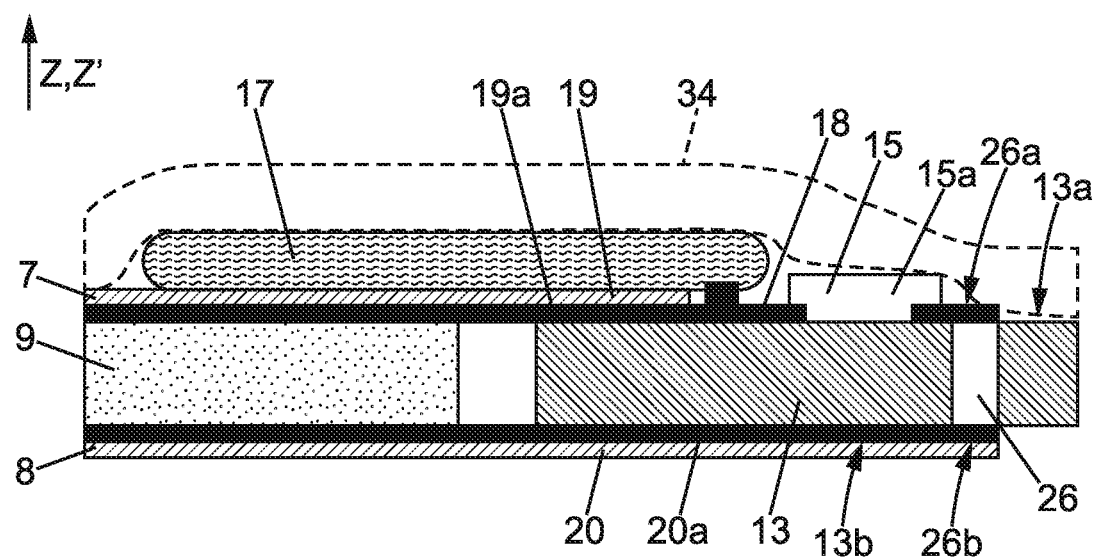
FIG. 11 is a detailed transverse section of a chip portion of a variant of the first embodiment of the insole of FIG. 5 showing in particular a battery and an upper contacting layer according to an embodiment of the invention.

Turning now to FIG. 11 which illustrates in particular an insole 1 with a battery 17 according to one embodiment of the invention, flexible battery 17 may in particular be a plane battery. The battery 17 may extend substantially along a first and a second perpendicular directions and have a smaller extension along a battery thickness direction Z', perpendicular to the first and the second directions.

As illustrated on FIG. 11, the battery 17 may be superimposed on the upper face 13a of the chip support member 13 so that the upper contacting tab 19 is at least partially sandwiched between the battery 17 and the upper face 13a of the chip support member 13.

In an alternative embodiment, the battery 17 may be superimposed on the lower face 13b of the chip support member 13 so that the lower contacting tab 20 is at least partially sandwiched between the battery 17 and the lower face 13b of the chip support member 13.

This way, the insole 1 can present a small thickness. Also, the comfort of the wearer is assured by laying the battery under a part of the foot that is naturally higher than the forefoot and the hindfoot.

As illustrated on FIG. 11, the insole may further be provided with an upper contacting layer 34. The upper contacting layer 34 may be arranged on top of the upper sheet 7 of the insole 1.

The upper contacting layer 34 is elastic and is adapted to be engaged by a foot of a wearer.

The upper sheet 7 of the insole 1 may thus be sandwiched between the upper contacting layer 34 and the dielectric sheet 9.

In the present description when reference is made to the upper insole surface 1a, it is meant the upper face of the insole in the absence of the upper contacting layer 34. The upper insole surface 1a is thus in contact with the bottom of the upper contacting layer 34.

With reference to FIG. 1, another object of the present invention is a system 1000 for monitoring a foot pressure.

The system 1000 comprises an insole 1 as described above.

System 1000 also comprises a remote server 100. The remote server 100 is able to receive pressure related data from the insole 1 by communicating with the wireless transceiver 16 of the insole 1.

The remote server 100 may for instance be a computer, a smartphone or the like with a wireless communication module.

The remote server 100 may be able to communicate over an extended network such as the internet in order to send the pressure related data and/or receive additional data from the network for post-processing.

By "pressure related data", it is meant data that are computed by the control electronic 15 on the basis of the measurements of the capacitive force sensors 10.

The invention claimed is:

1. An insole for insertion into an article of footwear, said insole being substantially planar and extending in an horizontal plane perpendicular to a thickness direction,
   the insole comprising a measurement portion extending in the horizontal plane,
   the measurement portion comprising at least:
      a flexible upper sheet and a flexible lower sheet facing one another in the thickness direction;
      a flexible insulating dielectric sheet arranged between the upper sheet and the lower sheet;
      a plurality of capacitive force sensors in the measurement portion of the insole, each capacitive force sensor comprising at least an upper electrode on the upper sheet and a lower electrode on the lower sheet, the lower electrode facing the upper electrode in the thickness direction and being separated from the lower electrode at least by the flexible insulating dielectric sheet;
      a network of upper conductive leads on the upper sheet, electrically connected to the upper electrodes of the plurality of capacitive force sensors, and a network of lower conductive leads on the lower sheet, electrically connected to the lower electrodes of the plurality of capacitive force sensors;
   wherein the insole further comprises a chip portion extending in the horizontal plane, the chip portion comprising at least:
      a chip support member being substantially planar and extending in the horizontal plane of the insole between an upper face and a lower face, said chip support member being separated from the dielectric sheet, and
      control and transmit electronics, mounted in the chip portion of the insole, and comprising at least a control electronic electrically connected to the plurality of capacitive force sensors and a wireless transceiver able to communicate with a remote server,
   wherein the upper sheet comprises an upper contacting tab extending from the measuring portion of the insole into the chip portion of the insole and being in surface contact with at least a portion of the chip support member, said upper contacting tab comprising at least one conductive lead connected to at least one upper electrode of a capacitive force sensor via the network of upper conductive leads, and
   the lower sheet comprises a lower contacting tab extending from the measuring portion of the insole into the chip portion of the insole and being in surface contact with at least a portion of the chip support member, said lower contacting tab comprising at least one conductive lead connected to at least one lower electrode of a capacitive force sensor via the network of lower conductive leads.

2. The insole according to claim 1,
   wherein the insole extends along a longitudinal direction and along a transverse direction perpendicular to said longitudinal direction, said longitudinal direction and said transverse direction belonging to the horizontal plane of the insole,
   wherein the insole has a length measured along the longitudinal direction and a width measured along transverse direction, the length of the insole being greater than the width of the insole,
   wherein the upper contacting tab of the upper sheet extends from the measuring portion of the insole into the chip portion of the insole substantially along the transverse direction, and
   wherein the lower contacting tab of the lower sheet extends from the measuring portion of the insole into the chip portion of the insole substantially along the transverse direction.

3. The insole according to claim 1, wherein the chip support member is separated from the dielectric sheet by a gap, a minimal width of said gap between the chip support member and the dielectric sheet, measured in the horizontal plane of the insole, being greater than 1 millimetre.

4. The insole according to claim 1, wherein the chip portion of the insole further comprises a casing, the casing covering at least a majority of the upper face of the chip support member and/or at least a majority of the lower face of the chip support member.

5. The insole according to claim 1, wherein the upper contacting tab of the upper sheet comprises at least one hole in the chip portion of the insole, and
   wherein the lower contacting tab of the lower sheet comprises at least one hole in the chip portion of the insole.

6. The insole according to claim 4, wherein the casing comprises at least one rod extending substantially along the thickness direction, said rod passing through said at least one hole of the upper contacting tab, through said at least one hole of the lower contacting tab, and through at least one hole of the chip support member.

7. The insole according to claim 2,
wherein the upper sheet comprises a plurality of upper contacting tabs extending from the measuring portion of the insole into the chip portion of the insole substantially along the transverse direction, and
wherein the lower sheet comprises a plurality of lower contacting tabs extending from the measuring portion of the insole into the chip portion of the insole substantially along the transverse direction, and
wherein the chip portion of the insole and the measurement portion of the insole are mechanically connected to one another solely via the plurality of upper contacting tabs and the plurality of lower contacting tabs.

8. The insole according to claim 7, wherein each upper contacting tab of the plurality of upper contacting tabs comprises at least one hole in the chip portion of the insole and
wherein each lower contacting tab of the plurality of lower contacting tabs comprises at least one hole in the chip portion of the insole.

9. The insole according to claim 4, wherein each upper contacting tab of the plurality of upper contacting tabs comprises at least one hole in the chip portion of the insole,
wherein each lower contacting tab of the plurality of lower contacting tabs comprises at least one hole in the chip portion of the insole, and
wherein the casing comprises a plurality of rods extending substantially along the thickness direction, each rod passing through at least one hole of an upper contacting tab of the plurality of upper contacting tabs, through at least one hole of a lower contacting tab of the plurality of lower contacting tabs, and through at least one hole of the chip support member.

10. The insole according to claim 4,
wherein the upper contacting tab of the upper sheet is at least partially covered by an upper thickening layer arranged on an upper face of the upper contacting tab of the upper sheet, wherein the lower contacting tab is at least partially covered by a lower thickening layer arranged on a lower face of the lower contacting tab of the lower sheet, and
wherein the upper thickening layer, the upper contacting tab, the chip support member, the lower contacting tab and the lower thickening layer are sandwiched between an upper retaining portion and a lower retaining portion of the casing.

11. The insole according to claim 6, wherein the casing comprises an upper casing portion and a lower casing portion assembled together and sandwiching the chip support member and the control and transmit electronics.

12. The insole according to claim 1, wherein the chip support member comprises a plurality of plated through holes.

13. The insole according to claim 12,
wherein each capacitive force sensor of the plurality of capacitive force sensors is associated with at least one plated through hole of the plurality of plated through holes, and
wherein each of said associated plated through holes is electrically connected,
to at least one pin of a chip of the control electronic, and
to at least one conductive lead connected to an associated electrode of the associated capacitive force sensor.

14. The insole according to claim 13,
wherein said chip of the control electronic is mounted on one of the upper surface and the lower face of the chip support member, and
wherein said conductive lead connected to an associated electrode of the associated capacitive force sensor is located on the other of said upper face and said lower face of the chip support member.

15. The insole according to claim 1, wherein the dielectric sheet is free of plated through holes.

16. The insole according to claim 1, wherein the upper contacting tab and the lower contacting tab are facing each other along the thickness direction, and wherein at least a portion of the chip support member is sandwiched between the upper contacting tab and the lower contacting tab.

17. The insole according to claim 1, wherein a lower face of the upper contacting tab is in surface contact with the upper face of the chip support member, and an upper face of the lower contacting tab is in surface contact with the lower face of the chip support member.

18. The insole according to claim 17, wherein the upper contacting tab and the lower contacting tab are respectively fixed to the upper face and the lower face of the chip support member, in particular are glued or laminated on said upper face and said lower face.

19. The insole according to claim 17, wherein
the upper contacting tab covers a majority of the upper face of the chip support member, and/or
the lower contacting tab covers a majority of the lower face of the chip support member.

20. A system for monitoring a foot pressure comprising:
an insole according to claim 1 and
a remote server able to communicate with the wireless transceiver of the insole to receive pressure related data from the insole.

21. The insole according to claim 3, wherein the minimal width of the gap is greater than 2 millimetres.

* * * * *